(12) United States Patent
Ukegawa

(10) Patent No.: US 9,186,693 B2
(45) Date of Patent: Nov. 17, 2015

(54) NOZZLE ASSEMBLY AND COMPOSITE STRETCH MATERIAL PRODUCED BY USING THE SAME

(75) Inventor: Kazuo Ukegawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 578 days.

(21) Appl. No.: 13/515,838

(22) PCT Filed: Dec. 16, 2010

(86) PCT No.: PCT/JP2010/072712
§ 371 (c)(1),
(2), (4) Date: Jun. 14, 2012

(87) PCT Pub. No.: WO2011/081032
PCT Pub. Date: Jul. 7, 2011

(65) Prior Publication Data
US 2012/0258277 A1  Oct. 11, 2012

(30) Foreign Application Priority Data
Dec. 28, 2009  (JP) .................... 2009-298165

(51) Int. Cl.
| | |
|---|---|
| *A61F 13/49* | (2006.01) |
| *A61F 13/491* | (2006.01) |
| *A61F 13/494* | (2006.01) |
| *A61F 13/496* | (2006.01) |
| *B05C 5/02* | (2006.01) |
| *B32B 5/02* | (2006.01) |
| *B32B 5/26* | (2006.01) |
| *B32B 7/12* | (2006.01) |
| *A61F 13/15* | (2006.01) |

(52) U.S. Cl.
CPC ........... *B05C 5/027* (2013.01); *A61F 13/15593* (2013.01); *B05C 5/0241* (2013.01); *B32B 5/022* (2013.01); *B32B 5/26* (2013.01); *B32B 7/12* (2013.01); *A61F 13/15* (2013.01); *B32B 2250/03* (2013.01); *B32B 2250/20* (2013.01); *B32B 2250/40* (2013.01); *B32B 2262/0207* (2013.01);

(Continued)

(58) Field of Classification Search
None
See application file for complete search history.

(56) References Cited

U.S. PATENT DOCUMENTS

| | | |
|---|---|---|
| 4,850,989 A | 7/1989 | Villez |
| 4,917,695 A | 4/1990 | Villez |
| 2004/0158217 A1 | 8/2004 | Wu et al. |

FOREIGN PATENT DOCUMENTS

| | | |
|---|---|---|
| EP | 0115286 A1 | 8/1984 |
| EP | 0984083 A2 | 3/2000 |

(Continued)

OTHER PUBLICATIONS

JP 2009-148447 Machine Translation via AIPN webiste.*

(Continued)

*Primary Examiner* — Mark Ruthkosky
*Assistant Examiner* — Laura C Powers
(74) *Attorney, Agent, or Firm* — Hauptman Ham, LLP

(57) ABSTRACT

A nozzle assembly includes an upstream block, an upstream shim, an intermediate shim, a downstream shim and a downstream block arranged in this order in a machine direction MD from the upstream side to the downstream side. A lower end of the nozzle is formed with grooves as guide grooves to support elastics. A first pipe, a dispersion slit for a web and convergence slits for a web define first flow channels wherein the slits are respectively formed with outlets for a web. A second pipe, a dispersion slit for elastics and convergence slits for elastics define a second flow channels wherein the slits are respectively formed with outlets for elastics. The outlets for elastics are formed in the respective guide grooves and each of the outlets for a web lies between each pair of the adjacent outlets for elastics as viewed in the cross direction CD.

2 Claims, 13 Drawing Sheets

(52) U.S. Cl.
CPC ......... *B32B 2307/51* (2013.01); *B32B 2555/02* (2013.01); *Y10T 428/24132* (2015.01)

(56) References Cited

FOREIGN PATENT DOCUMENTS

| | | |
|---|---|---|
| EP | 1440736 A2 | 7/2004 |
| JP | 61152801 | 7/1986 |
| JP | 63211302 | 9/1988 |
| JP | 01118606 | 5/1989 |
| JP | 2004352494 | 12/2004 |
| JP | 2009148447 | 7/2009 |

OTHER PUBLICATIONS

International Search Report for PCT/JP2010/072712 mailed Mar. 15, 2011.
Supplementary European Search Report issued Jun. 5, 2014, corresponds to European patent application No. 10840890.7.

* cited by examiner

FIG.10
(a)
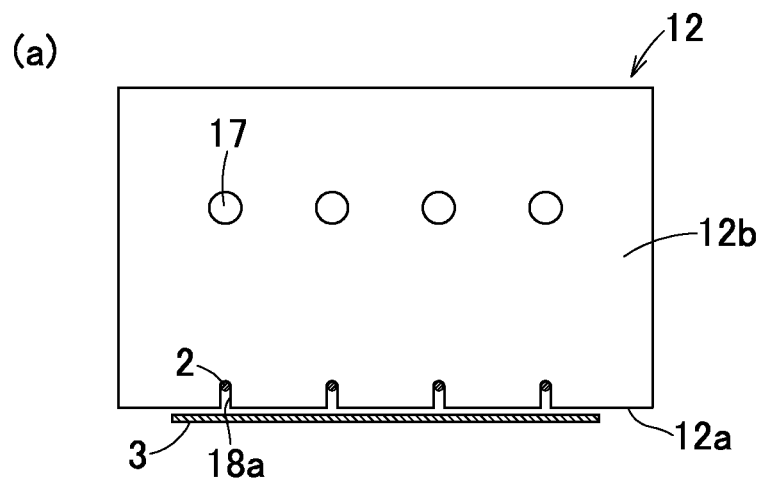
(b)
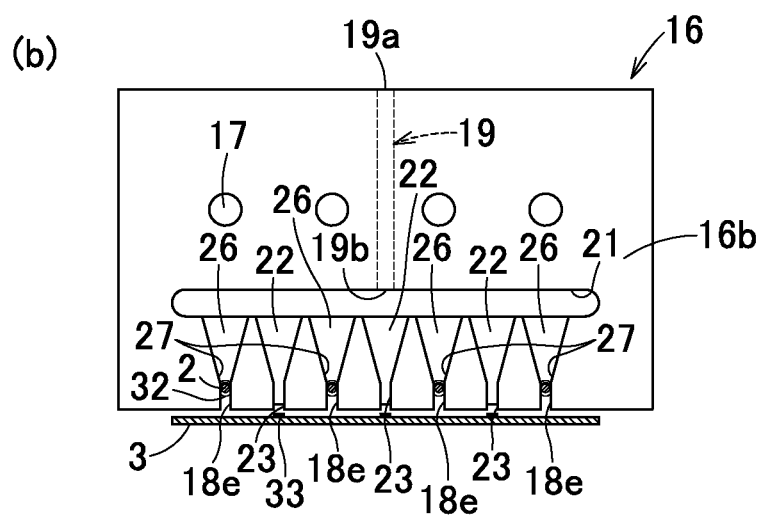

FIG.11
(a)
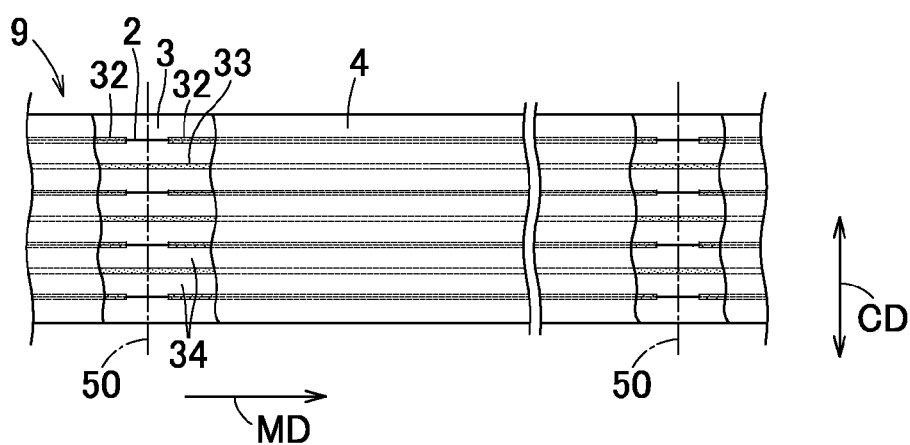
(b)
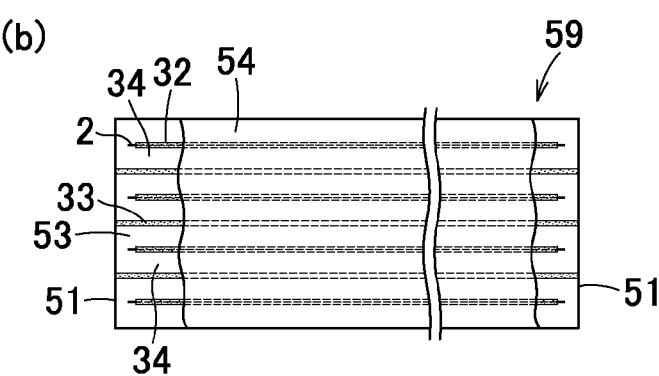

NOZZLE ASSEMBLY AND COMPOSITE STRETCH MATERIAL PRODUCED BY USING THE SAME

CROSS REFERENCE TO RELATED APPLICATIONS

This application is a national phase of PCT/JP2010/072712 filed Dec. 16, 2010 and is based on and claims priority from Japanese Application No. 2009-298165 filed Dec. 28, 2009.

TECHNICAL FIELD

The present invention relates to nozzle assemblies adapted to coat elastics such as elastic yarns or threads with adhesives such as hot melt adhesives and simultaneously adapted to coat sheets such as layers of fibrous nonwoven fabrics sandwiching elastics also with adhesives such as hot melt adhesives, and the present invention also relates to composite stretch materials produced by using such nozzle assemblies.

BACKGROUND

Nozzle assemblies which continuously coat the elastic yarns or threads continuously running in a machine direction with adhesives such as hot melt adhesives are known. For example, PTL 1 discloses a nozzle assembly adapted to coat the elastic yarns or threads with hot melt adhesives. The nozzle assembly disclosed therein includes slit-like guide grooves to guide the elastic yarns or threads to an adhesive outlet at respective nozzle ends and thereby coat the elastic yarns or threads with adhesives.

CITATION LIST

Patent Literature

{PTL 1} JP 2004-352494 A

SUMMARY

Technical Problem

PTL 1 discloses the nozzle assembly in the connection of its function to coat the elastic yarns or threads with adhesives but not of its function to coat the sheets sandwiching the elastic yarns or threads with adhesive so that these sheets and the elastic yarns or threads may be bonded together.

An object of the present invention is to provide a nozzle assembly adapted not only to coat elastics with adhesives but also to coat two layers of web material sandwiching these elastics with adhesives. Another object of the present invention is to provide a composite stretch material produced by using such nozzle assembly.

Solution to Problem

The present invention has a first aspect and a second aspect.

According to the first aspect of the present invention, there is provided a nozzle assembly adapted to coat a web having a first direction and a second direction orthogonal to the first direction with an adhesive and thereby to form adhesive lines for a web extending in the first direction and spaced one from another in the second direction and also to form adhesive lines for elastics adapted to coat elastics lying between the adhesive lines for a web or between imaginary extensions of the adhesive lines for a web.

The features according to the first aspect of the present invention resides in that: the nozzle assembly includes a supply port adapted to be supplied with the adhesive and outlets supplied with the adhesive via flow channels; the outlets includes outlets for a web adapted to form the adhesive lines for a web and outlets for elastics adapted to form the adhesive lines for elastics; the outlets for a web are formed at a nozzle bottom to be capable of contacting with a web; the outlets for elastics are formed in guide grooves which are formed in the nozzle bottom to guide elastics; each of the guide grooves lies between each pair of the adjacent outlets for a web and extends in the first direction; and the outlets for a web are spaced apart from the outlets for elastics in the second direction.

According to one embodiment of the present invention on the first aspect thereof, the nozzle assembly includes at least two or more outlets for a web and at least one or more outlets for elastics wherein the outlets for a web and the outlets for elastics are alternately arranged in the second direction.

According to another embodiment of the present invention on the first aspect thereof, the flow channels further include first flow channels fluid-communicating with the outlets for a web and second flow channels fluid-communicating with the outlets for elastics.

According to still another embodiment of the present invention on the first aspect thereof, the adhesive lines for a web are formed continuously in the first direction and the adhesive lines for elastics are formed intermittently in the first direction.

According to yet another embodiment of the present invention on the first aspect thereof, the nozzle assembly further includes an upstream block and a downstream block arranged in the first direction wherein these blocks may be subjected to cutting work to form the outlets for a web and the outlets for elastics and the flow channels fluid-communicating with the outlets for a web and the outlets for elastics.

According to further another embodiment of the present invention on the first aspect thereof, intermediate shims are arranged between the upstream block and the downstream block in the first direction in order to prevent fluid from moving between the upstream block and the downstream block.

According to the second aspect of the present invention, there is provided a composite stretch material having a longitudinal direction and a transverse direction and including: first and second sheets layered one another; and elastics attached under tension and in a contractible manner between the first and second sheets.

The features according to the second aspect of the present invention resides in that: the stretch composite material includes adhesive lines for a web adapted to join the first and second sheets together and extending in the longitudinal direction; and adhesive lines for elastics each extending in the longitudinal direction in parallel to the adhesive lines for elastics and overlapping with the elastics wherein the adhesive lines for a web and the adhesive lines for elastics are spaced one from another in the transverse direction to define non-coated regions coated with no adhesive between the adhesive lines for a web and the adhesive lines for elastics.

According to one embodiment of the present invention on the second aspect thereof, the first and second sheets respectively have opposite ends extending in the transverse direction and being spaced apart from each other in the longitudinal direction and the adhesive lines for a web fully extend from one of the ends to the other of the ends.

According to another embodiment of the present invention on the second aspect thereof, the adhesive lines for elastics and the elastics are formed so as to be spaced apart from at least one of the opposite ends.

Advantageous Effects of Invention

The nozzle assembly according to the present invention includes the outlets for elastics adapted to coat elastics with adhesive to form the adhesive lines for elastics and the outlets for a web adapted to coat a web with adhesive to form the adhesive lines for a web. With such an arrangement, the nozzle assembly may concurrently form the adhesive lines for a web and the adhesive lines for elastics.

BRIEF DESCRIPTION OF DRAWINGS

FIG. 10 is a plan view of each member in FIG. 9.

FIG. 11 is a diagram schematically illustrating a composite stretch material.

DESCRIPTION OF EMBODIMENTS

FIGS. 1 through 4 illustrate a nozzle assembly according to a first embodiment of the present invention.

Figure 1:
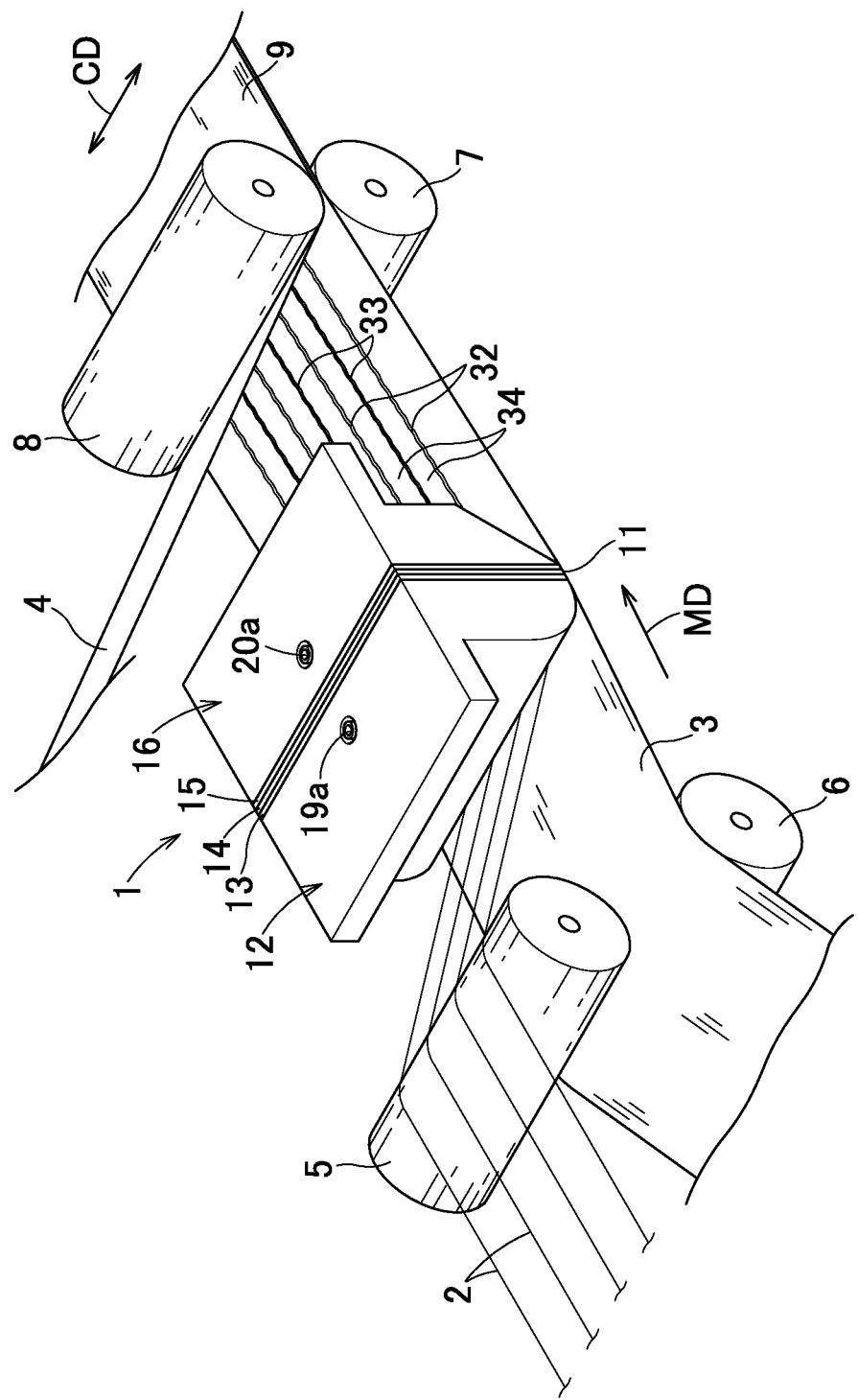
FIG. 1 is a schematic diagram illustrating the nozzle assembly operating for coating of adhesives.
Figure 2:
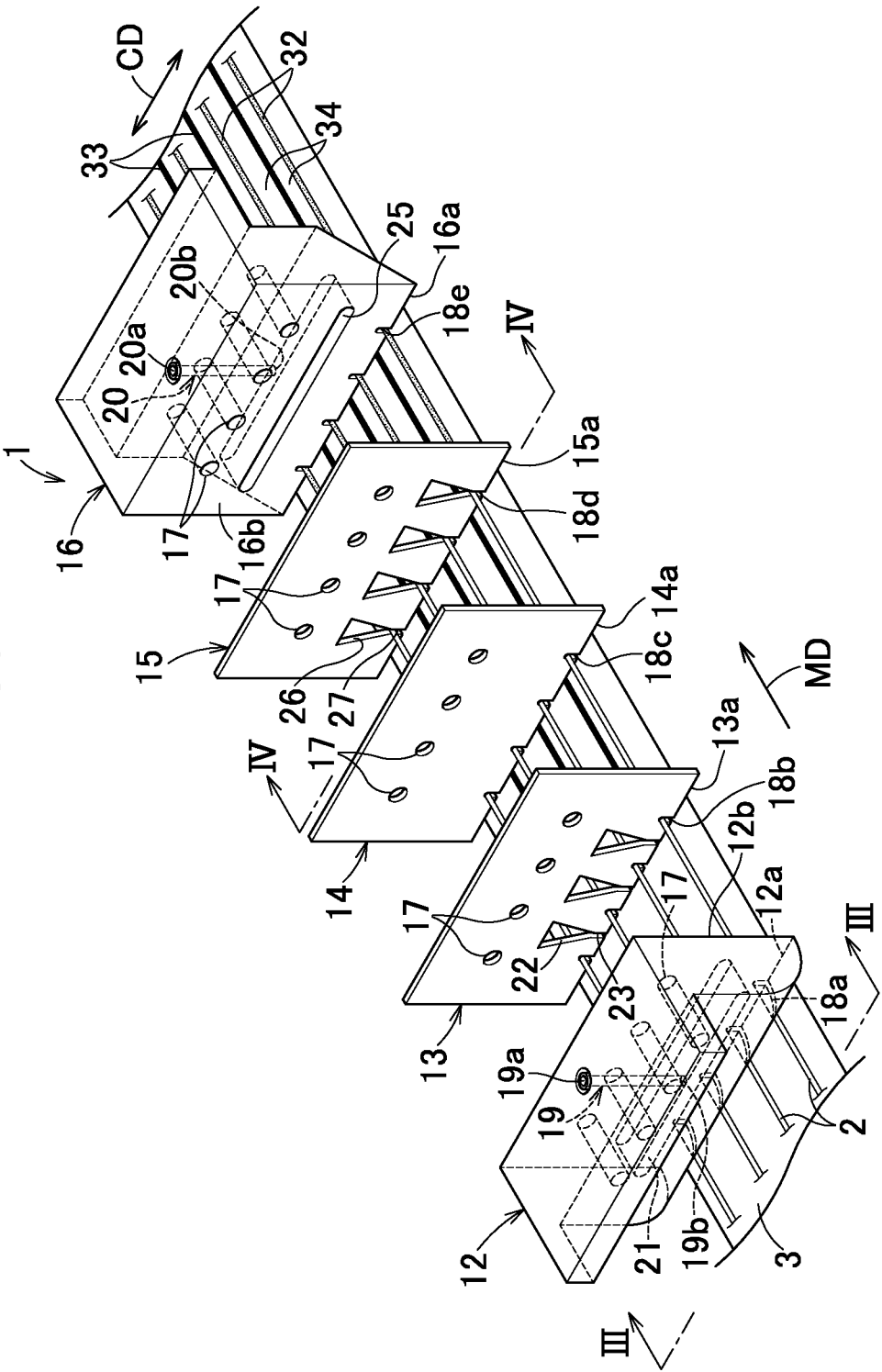
FIG. 2 is an exploded perspective view showing the nozzle assembly according to a first embodiment of the invention.
Figure 3:
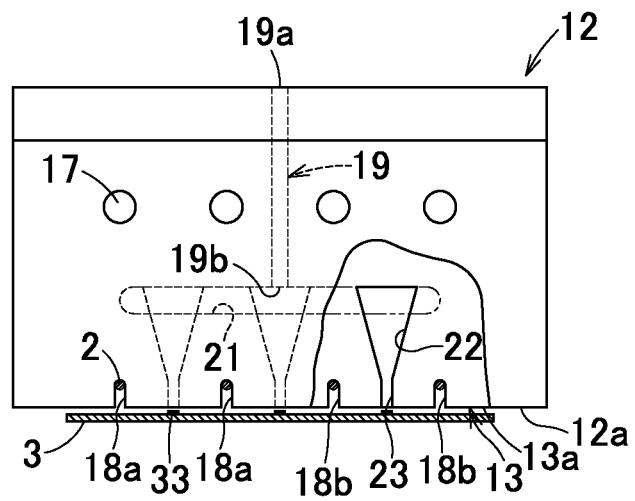
FIG. 3 is a sectional view taken along line III-III in FIG. 2.
Figure 4:
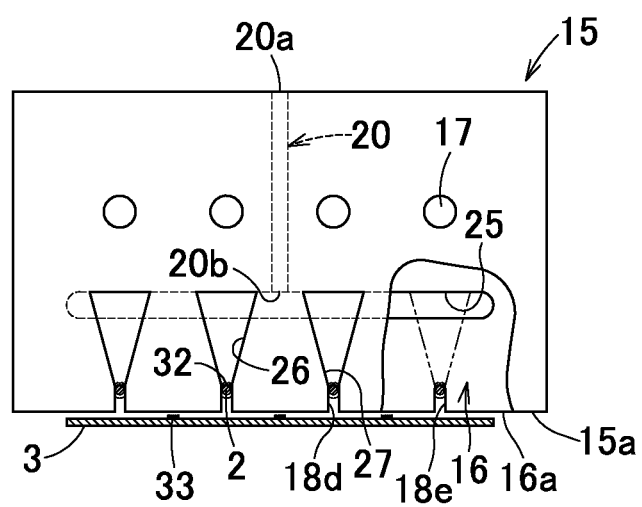
FIG. 4 is a sectional view taken along the line IV-IV in FIG. 2.

FIG. 1 is a perspective view schematically illustrating how the nozzle assembly 1 is used to coat elastics and a web of a fibrous nonwoven fabric with a hot melt adhesive, FIG. 2 is an exploded perspective view of the nozzle assembly 1, FIG. 3 is a sectional view taken along line III-III in FIG. 2 and FIG. 4 is a sectional view taken along line IV-IV in FIG. 2.

Referring to FIG. 1, the nozzle assembly 1 is fed with a plurality of elastics 2 kept at a predetermined stretch ratio via a first feed roller 5 and synchronously fed with a first web 3 formed of a fibrous nonwoven fabric kept at a predetermined tension via a second feed roller 6, both in a machine direction MD. In the nozzle assembly 1, the hot melt adhesive with which the elastics 2 have been coated forms a plurality of adhesive lines 32 for elastics 2 and the hot melt adhesive with which the first web 3 has been coated forms a plurality of adhesive lines 33 for a web. Each of the elastics 2 coated with the adhesive is arranged at least between each pair of the adjacent adhesive lines 33 for a web and, according to the present embodiment, the elastics 2 are arranged also further outer than the outermost adhesive lines 33 for a web. The elastics 2 coated with the adhesive in this manner are secured between a second web 4 and the first web 3 fed via a third roller 7 and a fourth roller 8. In this way, a composite stretch material 9 which is stretchable in the machine direction MD can be obtained. The composite stretch material 9 is formed by bonding the first and second webs 3, 4 to each other by the adhesive lines 32 for elastics and the adhesive lines 33 for a web. Between each pair of the adjacent adhesive lines 32 for elastics and adhesive lines 33 for a web, non-coated regions 34 which have been coated with no adhesive are formed.

As viewed in FIG. 1, the first feed roller 5 is located below the elastics 2 while the second feed roller 6 and the third roller 7 are located below the first web 3. The elastics 2 are kept in a tensioned state between the first feed roller 5 and the third roller 7 and between the third roller 7 and the fourth roller 8 in the course of being coated with the adhesive. The adhesive with which the elastics 2 are coated forms the adhesive lines 32 for elastics. The first web 3 is kept in a tensioned state between the second feed roller 6, the third roller 7 and the fourth roller 8 in the course of being coated with the adhesive discharged from outlets opening at a nozzle bottom 11. The adhesive with which the first web 3 is coated forms the adhesive lines 33 for a web. These first and second feed rollers 5, 6 may be designed to be movable in a vertical direction to space the elastics 2 and the first web 3 from the nozzle bottom 11. The elastics 2 as well as the first web 3 having been spaced from the nozzle bottom 11 in this manner are not coated with the hot melt adhesive.

In the construction as has been described above, a rate at which the elastics 2 are fed is substantially synchronized with a rate at which the first web 3 is fed. Consequently, the first web 3 and the elastics 2 are fed to the third roller 7 substantially at the same rate. On the third roller 7, the second web 4 is layered on the first web 3 by the intermediary of the elastics 2 and these webs 3, 4 and elastics 2 are bonded together by the third roller 7 and the fourth roller 8.

Referring to FIG. 2, the nozzle assembly 1 includes an upstream block 12, an upstream shim 13, an intermediate shim 14, a downstream shim 15 and a downstream block 16 arranged in this order from the upstream side to the downstream side in the machine direction MD. These blocks and shims are integrated in close contact with one another by inserting bolts (not shown) into a plurality of through-holes 17 of the respective blocks and shims and tightly fastening these blocks and shims together using nuts (not shown). The upstream shim 13, the intermediate shim 14 and the downstream shim 15 are formed of metallic plates.

The nozzle bottom 11 is formed with a plurality of guide grooves for the elastics 2 and, specifically, each of these guide grooves includes a groove 18a formed in a lower end 12a of the upstream block 12, a groove 18b formed in a lower end 13a of the upstream shim 13, a groove 18c formed in a lower end 14a of the intermediate shim 14, a groove 18d formed in a lower end 15a of the downstream shim 15 and a groove 18e formed in a lower end 16a of the downstream block 16 directly-aligned in the machine direction MD of the nozzle assembly 1.

The upstream block 12 and the downstream block 16 are respectively formed with a first pipe 19 and a second pipe 20 adapted to be supplied with a hot melt adhesive in a molten state. The first pipe 19 and the second pipe 20 respectively have ends 19a, 20a on one side opening in respective tops of the up- and downstream blocks 12, 16 and extend to respective interiors thereof in the vertical direction as viewed in FIG. 2. Supply tubes (not shown) to supply the hot melt adhesive in a molten state into the nozzle assembly 1 are connected to the ends 19a, 20a of the respective pipes 19, 20 and these ends 19a, 20a serve as supply ports for the adhesive.

The upstream block 12 is formed with a dispersion slit 21 for a web extending in a cross direction CD and this dispersion slit 21 for a web fluid-communicates with the other end 19b of the first pipe 19 to disperse the adhesive supplied to the first pipe 19 in the cross direction CD. The dispersion slit 21 for a web is opened toward a downstream side 12b of the upstream block 12 facing the intermediate shim 14.

The upstream shim 13 is formed with a plurality of substantially triangular convergence slits 22 for a web, which extend through the shim 13 in its thickness direction. Specifically, the upstream shim 13 is formed with three such convergence slits 22 for a web being spaced one from another in the cross direction CD. Each of these substantially triangular convergence slits 22 for a web has its apex pointing to a lower end 13a of the upstream shim 13 and the lower end 13a thereof is formed with an outlet 23 for a web which fluid-communicates with the convergence slit 22 for a web.

The intermediate shim 14 is formed with nothing but the grooves 18c and the through-holes 17, and the intermediate shim 14 closes off the convergence slits 22 for a web and the outlets 23 for a web of the upstream shim 13 from the downstream side thereof.

FIG. 3 is a sectional view taken along line III-III in FIG. 2 in which the upstream block 12 overlap with the upstream shim 13 wherein the upstream shim 13 is partially cutaway for convenience of illustration and the first web 3 is spaced downward from the respective lower ends 12a and 13a. In an overlapped state, the upstream block 12 and the upstream shim 13 respectively have the dispersion slit 21 for a web and the convergence slits 22 for a web partially overlapping one another. With such an arrangement, the adhesive supplied through the first pipe 19 is guided by the dispersion slit 21 for a web so as to flow into the respective convergence slits 22 for a web. The convergence slits 22 for a web formed in the upstream shim 13 are closed off by the intermediate shim 14 so that the first pipe 19, the dispersion slit 21 for a web and the convergence slits 22 for a web may define first flow channel. The first flow channel fluid-communicates with the respective outlets 23 for a web, allowing the adhesive to be supplied to the respective outlets 23 for a web. The adhesive supplied to the respective outlets 23 for a web is applied to the first web 3 running in contact with the lower end 13a and thereby the adhesive lines 33 for a web are formed.

The grooves 18a formed in the upstream block 12 and the grooves 18b formed in the upstream shim 13 are directly-aligned in the machine direction MD between each pair of the adjacent outlets 23 for a web. With such an arrangement, the elastics 2 running through the guide grooves defined by these grooves 18a, 18b are free from being coated with the adhesive discharged from the respective outlets 23 for a web. Furthermore, in the upstream shim 13 formed with the outlets 23 for a web, the elastics 2 are spaced upward as viewed in FIG. 3 from the lower end 13a so that the first web 3 may come in contact with the lower end 13a without being interrupted by elastics 2. In this way, the outlets 23 for a web formed along the lower end 13a ensure the first web 3 to be reliably formed with the adhesive lines 33 for a web.

At least in a region overlapping the adhesive lines 33 for a web, the lower end 14a of the intermediate shim 14, the lower end 15a of the downstream shim 15 and the lower end 16a of the downstream block 16 preferably lie above the lower end 12a of the upstream block 12 and the lower end 13a of the upstream shim 13 as viewed in FIG. 3. This is for the purpose of preventing the adhesive discharged from the outlets 23 for a web of the upstream shim 13 from adhering to the intermediate shim 14, the downstream shim 15 and the downstream block 16 lying on a downstream side of the lower ends 12a, 13a.

Referring again to FIG. 2, the downstream block 16 is formed with a dispersion slit 25 for elastics extending in a cross direction CD and fluid-communicating with the other end 20b of the second pipe 20 to disperse the adhesive supplied to the second pipe 20 in the cross direction CD. The dispersion slit 25 for elastics is opened in the upstream side 16b facing the downstream shim 15.

The downstream shim 15 is formed with a plurality of substantially triangular convergence slits 26 for elastics which extend through the shim 15 in its thickness direction. Specifically, the downstream shim 15 is formed with four such convergence slits 26 for elastics spaced one from another in the cross direction CD. Each of these substantially triangular convergence slits 26 for elastics has its apex pointing to a lower end 15a of the upstream shim 15 and the lower end 15a thereof is formed with grooves 18d. These grooves 18d fluid-communicate with the associated convergence slits 26 to define outlets 27 for elastics. It should be appreciated that the convergence slits 26, the outlets 27 for elastics and the grooves 18d are integrated according to the present embodiment. The convergence slits 26 and the outlets 27 for elastics are closed off on the upstream side by the intermediate shim 14.

As viewed in the cross direction CD, each of the outlets 23 for a web lies between each pair of the adjacent outlets 27 for elastics. In other words, the outlet 23 for a web and the outlet 27 for elastics are spaced apart from each other in the cross direction CD.

FIG. 4 is a sectional view taken along line IV-IV in FIG. 2 in which the downstream shim 15 overlap with the downstream block 16 wherein the downstream shim 15 is partially cutaway for convenience of illustration and the first web 3 is spaced downward from the respective lower ends 15a and 16a. In the overlapped state, the downstream block 16 and the downstream shim 15 respectively have the convergence slits 26 for elastics and the dispersion slits 25 for elastics overlapping one another. With such an arrangement, the adhesive supplied to the second pipe 20 is guided by the dispersion slit 25 for elastics so as to flow into the respective convergence slits 26 for elastics. The convergence slits 26 for elastics formed in the downstream shim 15 are closed off by the intermediate shim 14 so that the second pipe 20, the dispersion slit 25 for elastics and the convergence slits 26 for elastics may define a second flow channel. The adhesive supplied through the second flow channel flows into the convergence slits 26 for elastics and then discharged from the outlets 27 for elastics intermittently formed along the lower end 15a. More specifically, the respective outlets 27 for elastics are formed in the respective guide grooves 18d, allowing elastics 2 to be coated with the adhesive while they are guided by the grooves 18d. In this way, the adhesive lines 32 for elastics are formed.

The elastics 2 are fed along the guide grooves defined by the grooves 18a-18e and coated with the adhesive by the outlets 27 for elastics opening in the respective guide grooves. Specifically, the outlets 27 for elastics lie above the lower end 15a, i.e., the nozzle bottom 11 as viewed in FIG. 4. In contrast, the first web 3 are fed along the lower end 15a, i.e., the nozzle bottom 11. In consequence, on the lower end 15a of the downstream shim 15, elastics 2 are exclusively coated with the adhesive and the adhesive discharged from the outlets 27 for elastics should not adhere to the first web 3.

The guide grooves defined by the grooves 18a-18e are directly aligned in the machine direction MD of the nozzle assembly 1 and therefore the elastics 2 can be fed without being displaced in the cross direction CD. It should be noted here that the elastics 2 are guided by the grooves 18a-18c located on the upstream side of the outlets 27 for elastics in the machine direction MD, but after being coated with the adhesive by the outlets 27 for elastics formed in the respective grooves 18d, the elastics 2 are moved downward as viewed in FIG. 4 so as not to contact with the downstream grooves 18e. This is for the purpose of preventing the adhesive coated to the elastics 2 from adhering to these grooves 18e.

The outlet 23 for a web and the outlet 27 for elastics are spaced from each other in the cross direction CD and therefore the adhesive lines 33 formed on the first web 3 by the outlet 23 for a web should not overlap the elastics 2 coated by the outlet 27 for elastics, i.e., the adhesive lines 32 for elastics. In other words, each of the adhesive lines 33 for a web is formed between each pair of the adjacent adhesive lines 32 for elastics. Therefore, non-coated regions 34 which have been coated with no adhesive are formed between the adhesive lines 32 for elastics and the adhesive lines 33 for a web (See FIGS. 1 and 2). The formation of such non-coated regions 34 makes it possible to prevent stiffness of the first and second webs 3, 4 from increasing and, at the same time, to ensure the breathability of the first and second webs 3, 4.

As has been described above, the nozzle assembly 1 according to the present invention allows the outlets 23 for a web located on the upstream side of the assembly 1 to form the adhesive lines 33 for a web and the outlets 27 for elastics located on the downstream side of the assembly 1 to form the adhesive lines 32 for elastics. Compared to the case in which a web and elastics are coated with adhesives using different nozzle assemblies, a time lag between two separate operations of adhesive coating can be significantly reduced. In this way, the present invention can prevent displacement of the elastics 2 in the cross direction CD relative to the first web 3 which would become remarkable when the time lag is large.

With a unique arrangement that the first pipe 19 fluid-communicates with the outlets 23 for a web via the first flow channel and the second pipe 20 fluid-communicates with the outlets 27 for elastics via the second flow channel, the first pipe 19 and the second pipe 20 may be used to supply the adhesive of different types. For example, adhesives suitable for elastics and adhesives suitable for fibrous nonwoven fabrics may be separately used.

While a supply pipe (not shown) connected to the nozzle assembly 1 includes a heater and a pump so that the hot melt adhesive may be fed in a molten state at a desired temperature, such heater and pump are not illustrated in FIGS. 1 through 4. The nozzle assembly 1 is preferably incorporated with the heater so that the nozzle assembly 1 may be partially or wholly temperature-controlled.

In the nozzle assembly exemplarily illustrated, the respective shims 13, 14, 15 may be formed of a metallic sheet significantly thinner than the upstream block 12 as well as the downstream block 16. For example, the upstream block 12 and the downstream block 16 may be formed of iron blocks each having a thickness in the machine direction MD in a range of 20 to 200 mm and the respective shims 13, 14, 15 may be formed by partially cutting out iron sheets each having a thickness in the machine direction MD in a range of 0.2 to 3 mm. The nozzle assembly 1 using such thin iron sheets allows the intervals at which the adhesive lines are arranged and the width of the respective adhesive lines to be changed promptly and at low cost.

The hot melt adhesive may be replaced by the other types of adhesives such as solvent type adhesives. Material of the first and second webs 3, 4 are not limited to fibrous nonwoven fabrics but the other sheet-like materials such as woven fabrics, papers and plastic films may be also used. It is not essential to form a plurality of the adhesive lines 32 for elastics and to form a plurality of the adhesive lines 33 for a web but these may be respectively formed as a single line depending on circumstances.

Figure 5:
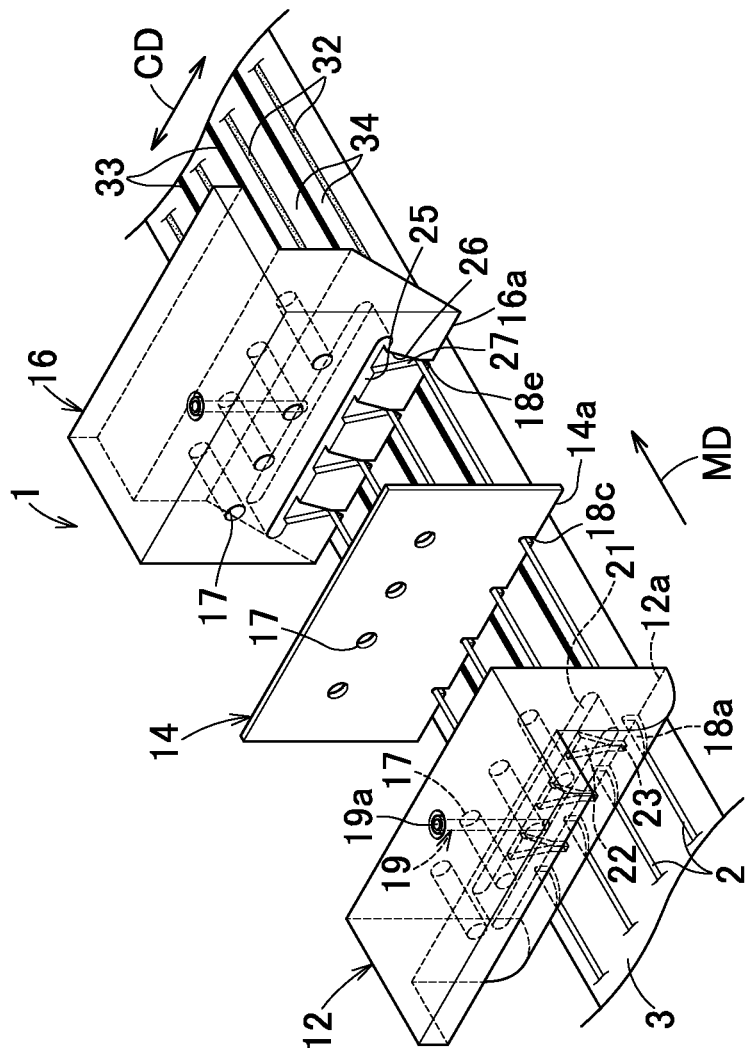
FIG. 5 is an exploded perspective view showing the nozzle assembly according to a second embodiment of the invention.
Figure 6:
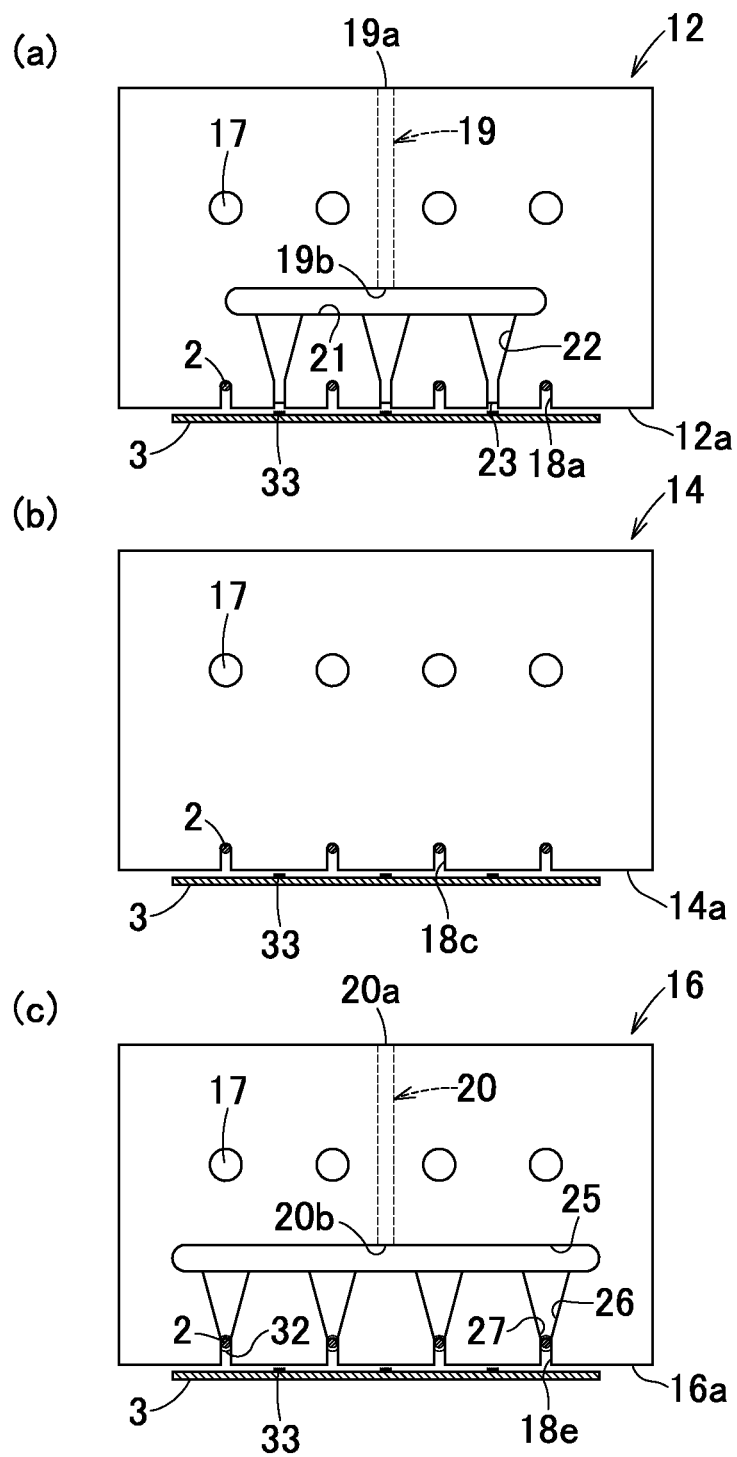
FIG. 6 is a plan view of each member in FIG. 5.

FIGS. 5 and 6 illustrate the nozzle assembly 1 according to the second embodiment of the present invention wherein FIG. 5 is an exploded perspective view similar to FIG. 2, FIG. 6(a) is a plan view of the upstream block 12 as viewed from the downstream side 12b thereof, FIG. 6(b) is a plan view of the intermediate shim 14 and FIG. 6(c) is a plan view of the downstream block 16 as viewed from the upstream side 16b thereof.

The nozzle assembly 1 is characterized in that the upstream block 12 is formed with the first pipe 19, the dispersion slit 21 for a web, the convergence slit 22 for a web and the outlets 23 for a web defining together the first flow channel. The nozzle assembly 1 is characterized also in that the downstream block 16 is formed with the second pipe 20, the dispersion slit 25 for elastics, the convergence slits 26 for elastics and the outlets 27 for elastics defining together the second flow channel. The intermediate shim 14 lies between these upstream block 12 and downstream block 16 to partition the first flow channel and the second flow channel off from each other. The other features are similar to those of the nozzle assembly 1 according to the first embodiment as illustrated in FIGS. 1 through 4.

In this nozzle assembly according to the second embodiment, the first flow channel and the outlets 23 for a web are formed in the upstream block 12 and thereby the number of the shims may be reduced in comparison to the case in which the slits 21, 22 are respectively formed in the separate shims. This is true for the second flow channel. In a similar fashion, the slits 25, 26 are formed in the downstream block 16 and thereby the number of the shims may be reduced in comparison to the case in which these slits 25, 26 are formed in the separate shims. Specifically, the upstream shim as well as the downstream shim in the nozzle assembly 1 according to the first embodiment may be eliminated. In this way, the number of parts may be reduced and the nozzle assembly can be downsized.

Figure 7:
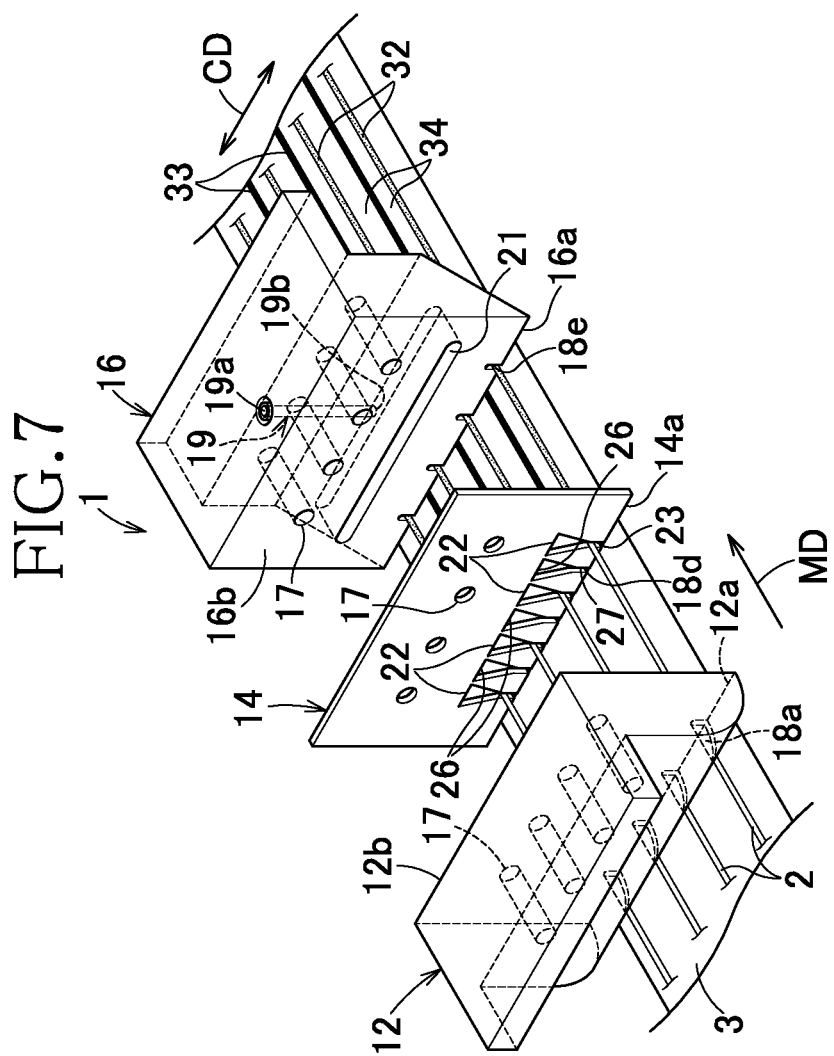
FIG. 7 is an exploded perspective view showing the nozzle assembly according to a third embodiment of the invention.
Figure 8:
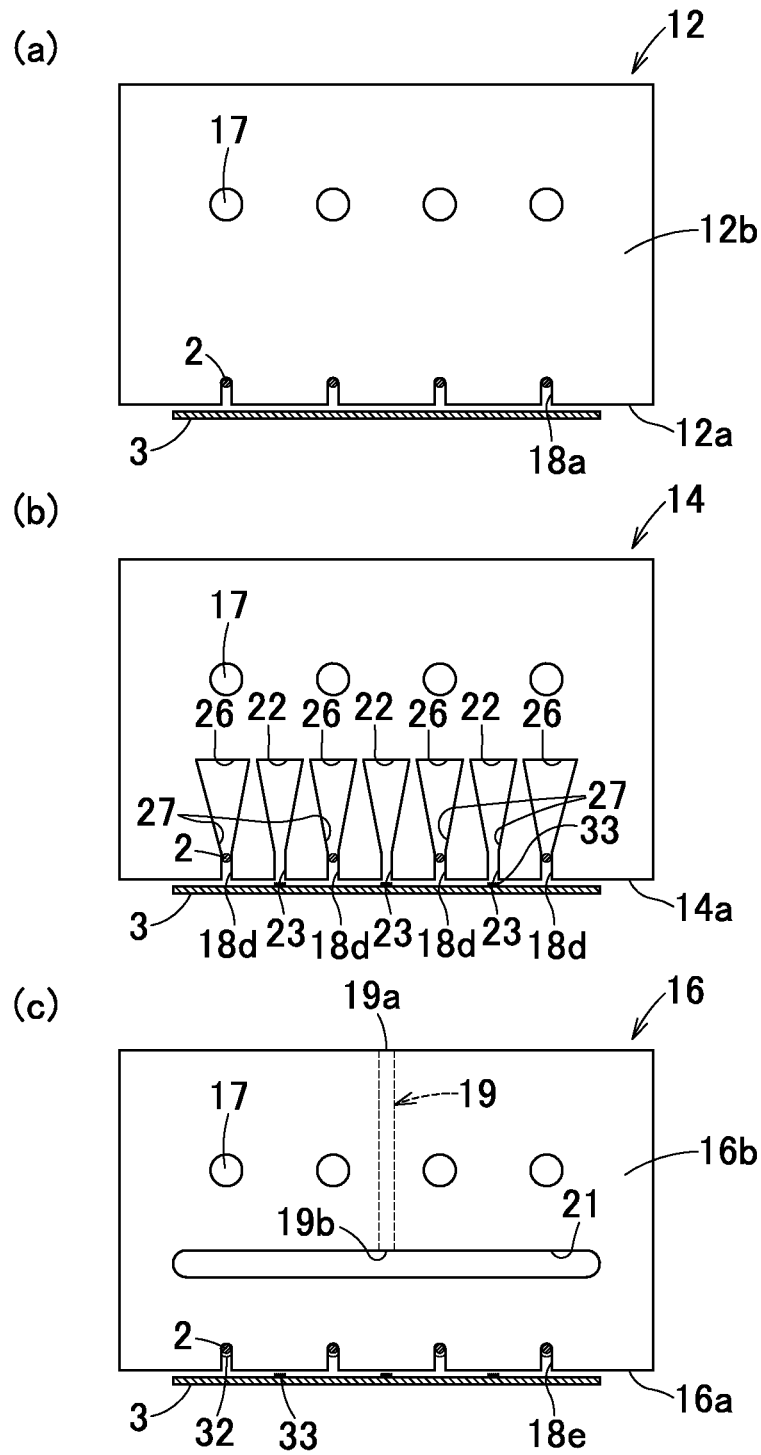
FIG. 8 is a plan view of each member in FIG. 7.

FIGS. 7 and 8 illustrate the nozzle assembly 1 according to the third embodiment of the present invention wherein FIG. 7 is an exploded perspective view, FIG. 8(a) is a plan view of the upstream block 12 as viewed from the downstream side 12b thereof, FIG. 8(b) is a plan view of the intermediate shim 14 and FIG. 8(c) is a plan view of the downstream block 16 as viewed from the upstream side 16b thereof.

The nozzle assembly 1 according to this embodiment is characterized in that respective functions of the first and second flow channel in the first and second embodiments are achieved by a single flow channel and the hot melt adhesive is supplied through this single flow channel to the outlets for a web and the outlets for elastics. The other features are similar to those in the nozzle assembly according to the first embodiment.

In the nozzle assembly 1 according to the present embodiment, the downstream block 16 is formed with the first pipe 19 used to supply the adhesive and with the dispersion slit 21 for a web fluid-communicating with the first pipe 19. The upstream block 12 is formed with neither a pipe nor a slit. The intermediate shim 14 lying between the upstream block 12 and the downstream block 16 is alternately formed with the convergence slit 22 for a web fluid-communicating with the dispersion slit 21 for a web and the convergence slits 26 for elastics. The respective convergence slits 22 for a web are formed with the outlets 23 for a web opening in the lower end 14a and the convergence slits 26 for elastics are formed with the outlets 27 for elastics opening in the lower end 14a. The outlets 27 for elastics are aligned with the guide grooves for elastics 2 but the outlets 23 for a web are not aligned with the guide grooves.

The adhesive supplied to the first pipe 19 is further supplied through the convergence slit 22 for a web, the dispersion slit 21 for a web, the convergence slits 22 for a web and the convergence slits 26 for elastics to the outlets 23 for a web and the outlets 27 for elastics. In this way, the formation of the adhesive lines 33 on the first web 3 and the formation of the adhesive lines 32 for elastics by coating elastics 2 with the adhesive can be concurrently progressed.

Figure 9:
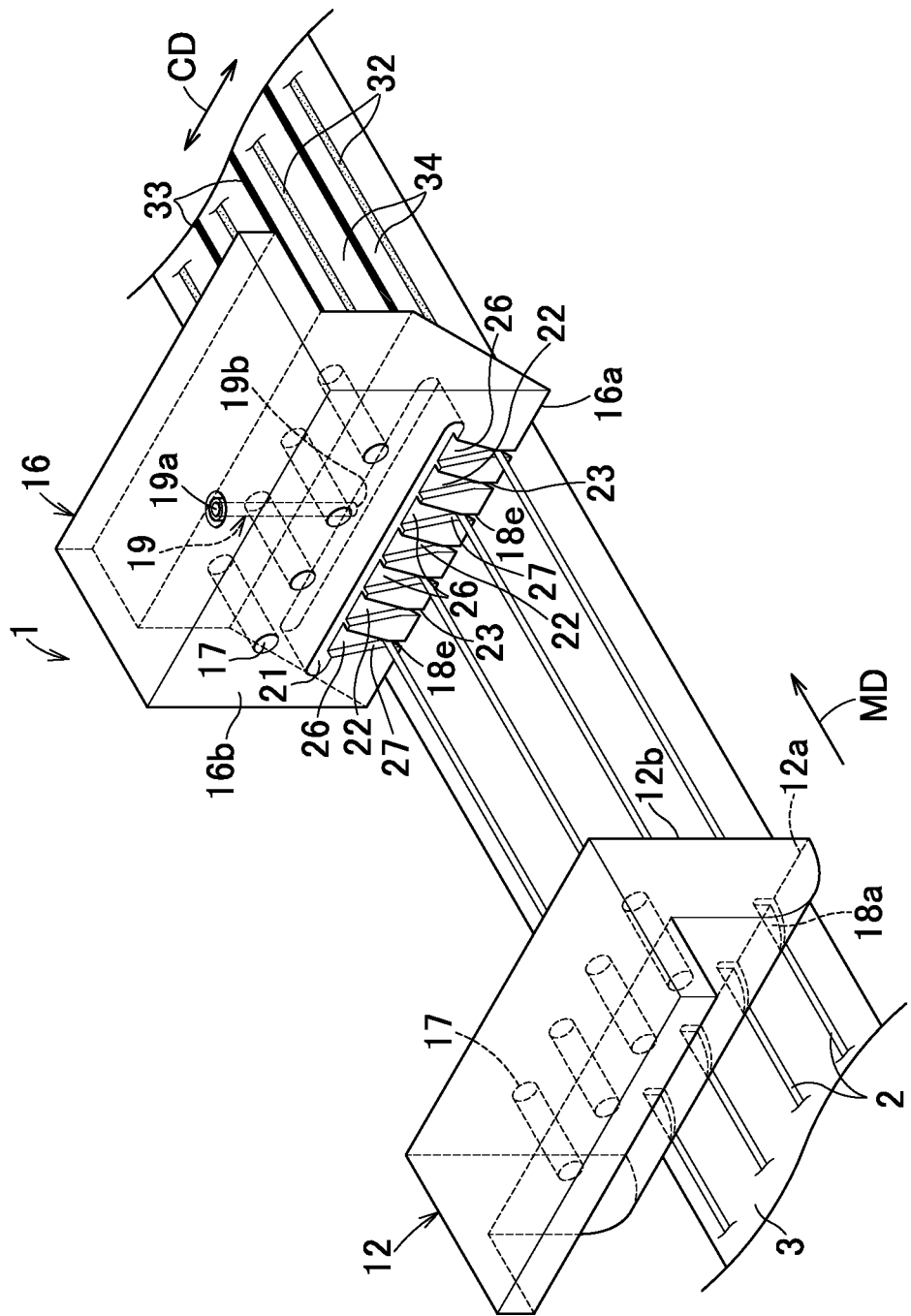
FIG. 9 is an exploded perspective view showing the nozzle assembly according to a fourth embodiment of the invention.

FIGS. 9 and 10 illustrate the nozzle assembly 1 according to the fourth embodiment of the present invention wherein FIG. 9 is an exploded perspective view of the nozzle assembly 1, FIG. 10(a) is a plan view of the upstream block 12 as viewed from the downstream side 12b thereof and FIG. 10(b) is a plan view of the downstream block 16 as viewed from the upstream side 16b thereof.

The nozzle assembly 1 according to the present embodiment is similar to the nozzle assembly 1 according to the third embodiment in which the respective functions of the first and second flow channels can be fulfilled by the single flow channel but distinguished from the nozzle assembly 1 according to the third embodiment in which the convergence slit 22 for a web, the convergence slit 26 for elastics, the outlets 23 for a web and outlets 27 for elastics are formed in the downstream block 16. The other features are similar to those in the nozzle assembly 1 according to the third embodiment. It is unnecessary for the nozzle assembly according to this embodiment to use any shim and the nozzle assembly 1 may be correspondingly downsized.

FIG. 11 illustrates a stretch composite material 9 made by using the nozzle assembly as has been described hereinabove wherein FIG. 11(a) illustrates a continuous stretch composite material 9 and FIG. 11(b) illustrates a stretch sheet 59 cut from the continuous stretch composite material 9 and partially cutaway for convenience of illustration.

Referring to FIG. 11(a), the first web 3 is formed with the adhesive lines 33 for a web of which the number corresponds to the number of the outlets for a web and these adhesive lines 33 for a web are continuously formed without interruption in the machine direction MD. Between the adhesive lines 33 in the cross direction CD, the elastics 2 are attached to the first web 3 under tension and in a contractible manner in the machine direction MD and the adhesive lines 32 are formed by the adhesive applied to the elastics 2. The adhesive lines 32 are formed intermittently formed in the machine direction MD. In other words, the elastics 2 are partially free from being coated with the adhesive and, in consequence, the adhesive lines 32 for elastics are partially interrupted.

The intermittent formation of the adhesive lines 32 for elastics may be achieved by intermittently supplying the adhesive from the pipe. The adhesive lines 33 for a web are continuously formed while the adhesive lines 32 for elastics are intermittently formed by continuously supplying the adhesive from the outlets for a web and simultaneously by intermittently supplying the adhesive from the outlets for elastics. The continuous adhesive lines and the intermittent adhesive lines may be concurrently formed only by using the nozzle assembly according to the first or second embodiment as has been described above, in other words, only when the first and second pipes are connected to the outlets for a web and to the outlets for elastics, respectively, so that supply from these two pipes may be separately controlled.

The continuous stretch composite material 9 is cut along cutting lines 50 in regions of the material 9 in which the adhesive lines 32 for elastics are interrupted. The cutting lines 50 extend in the cross direction CD and cutting the stretch composite material 9 may cut along these cutting lines 50 to obtain a stretch sheet 59 having cut edges 51 along which none of the elastics 2 are present. In the regions where all elastics 2 are not coated with the adhesive, the elastics 2 contract inward from the cutting edges 51 under contractile force thereof to be so-called cut back. As a result, none of the elastics 2 are present in the vicinities of the cut edges 51.

The adhesive lines 33 for a web continuously formed remain in the cut edges even after having been cut along the cutting lines 50. In consequence, as will be apparent from FIG. 11(b), a first sheet 53 formed of the first web 3 and a second sheet 54 formed of the second web 4 remain bonded to each other with the adhesive lines 33 for a web in the vicinities of the cut edges 51. Such stretch sheet 59 contract in the machine direction MD in which the elastics 2 extend.

According to the present embodiment, each of the adhesive lines 32 is formed between each pair of the adjacent adhesive lines 33 for a web. In other words, the adhesive lines 33 for a web and the adhesive lines 32 for elastics are alternately formed in the cross direction CD. When the elastics 2 are so-called cut back, the segments coated with no adhesive smoothly contract in the machine direction MD but if the two adhesive lines 33 for a web are not present on both sides of the respective elastics 2, the elastics 2 having been cut back might often be curled up or buckled up, deteriorating the appearance of the stretch sheet 59. However, according to the present embodiment, each pair of the adjacent adhesive lines 33 for a web may be arranged both sides of the segment of the elastics 2 not coated with the adhesive to ensure such segment of the elastics 2 to contract linearly between the adhesive lines 33 for a web and to maintain a neat appearance.

Figure 12:
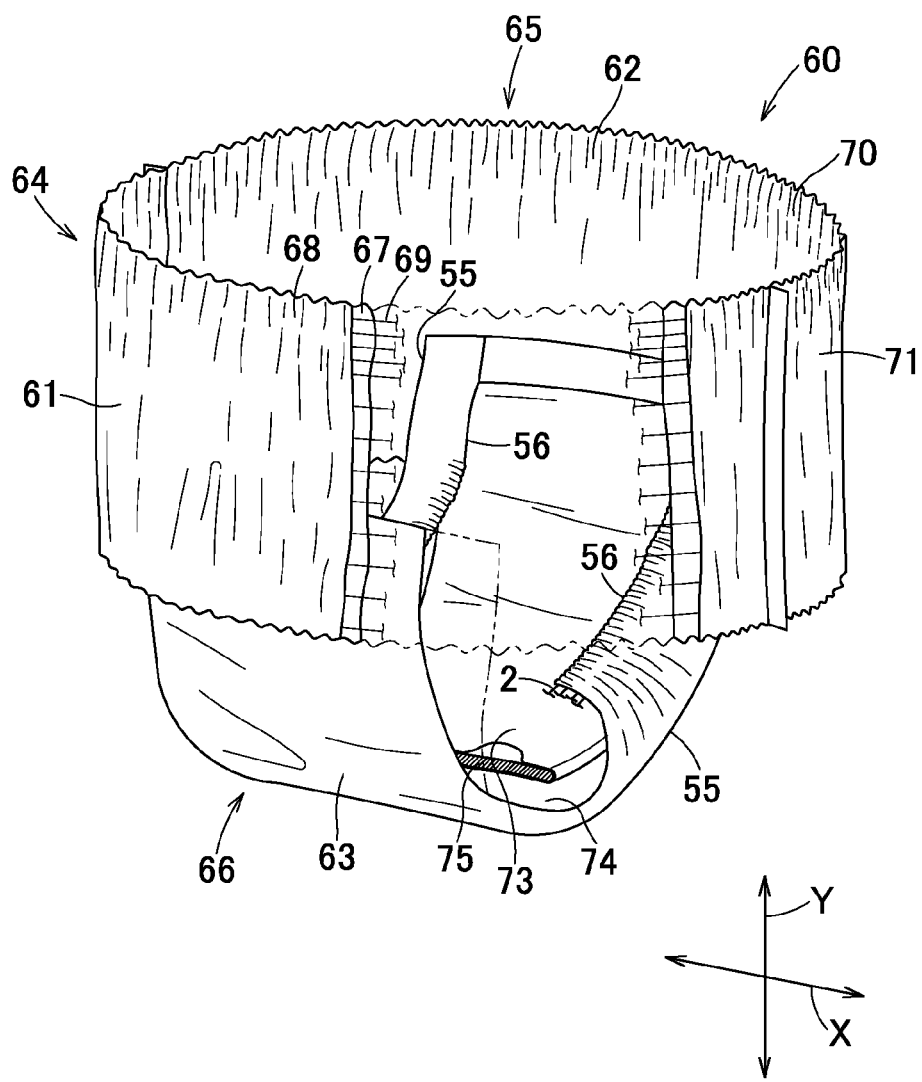
FIG. 12 is a perspective view of the diaper.
Figure 13:
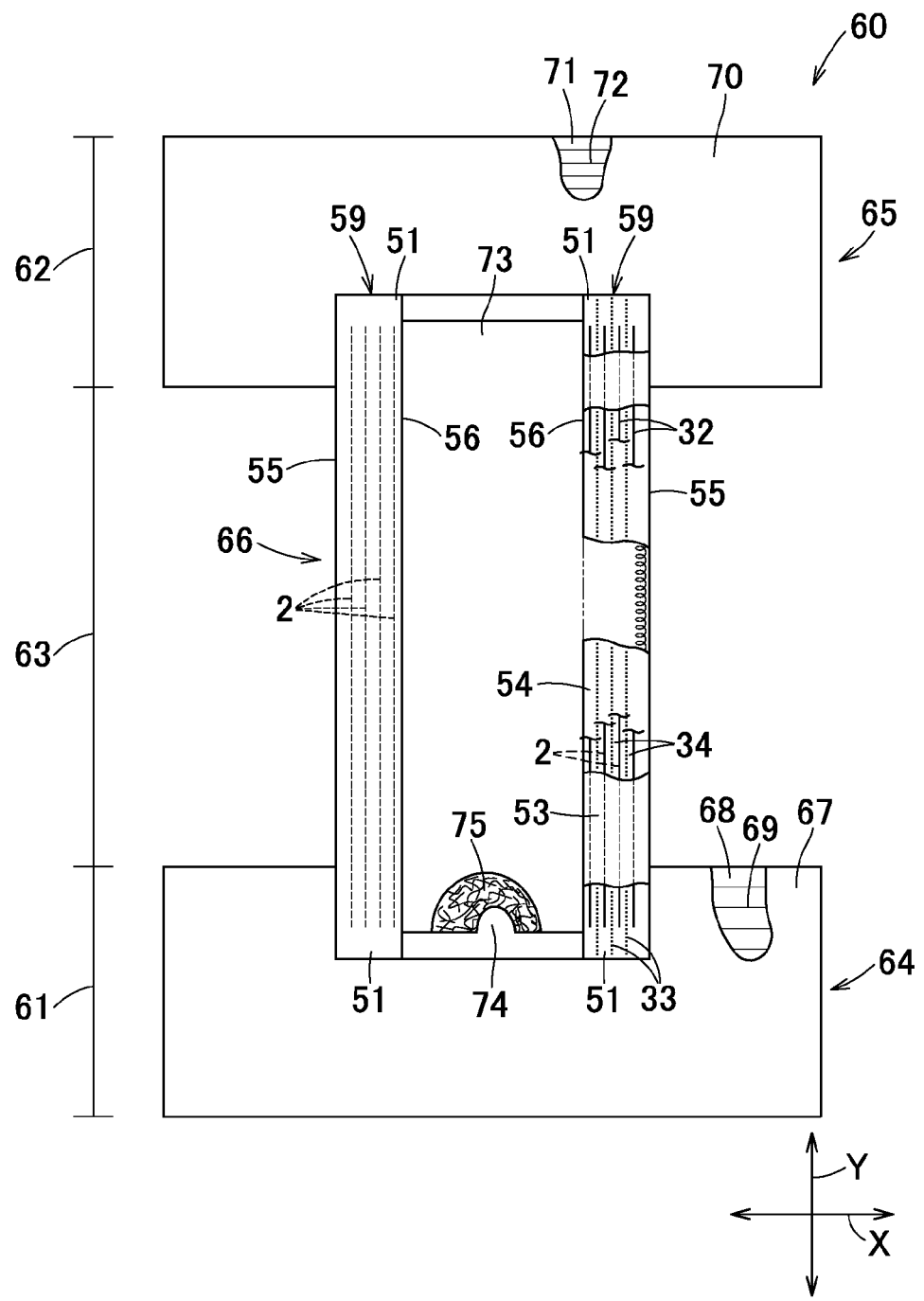
FIG. 13 is a plan view showing the diaper as developed and flattened.

FIGS. 12 and 13 illustrate a disposable diaper 60 using the stretch composite sheet 59 as leakage-barrier cuffs. FIG. 12 is a perspective view of the diaper 60 as its waist-opening kept in an annular state and FIG. 13 is a plan view of the diaper 60 as developed and flattened against contractile force of respective elastic members.

The diaper 60 has a longitudinal direction Y, a transverse direction X, a side facing the wearer's body and a side facing the wearer's garment and includes a front waist region 61, a rear waist region 62 and a crotch region 63 extending between these front and rear waist regions 61, 62 so as to be contiguous to one another in the longitudinal direction Y. The front waist region 61 is defined by a front waist member 64, the rear waist region 62 is defined by a rear waist member 65 and the crotch region 63 is defined by a crotch member 66. The respective members 64, 65, 66 cooperate with one another to define a chassis so called in the present invention.

The front waist region 64 includes an inner sheet 67 defining a body-facing side facing the wearer's body, an outer sheet 68 defining a garment-facing side facing the wearer's garment and waist elastics 69 interposed between these inner and outer sheets 67, 68. In a similar fashion, the rear waist region 65 includes an inner sheet 70 defining the body-facing side, an outer sheet 71 defining the garment-facing side and waist elastics 72 interposed between these inner and outer sheets 70, 71. The waist elastics 69, 72 extend in the transverse direction X and attached under tension and in a contractible manner. The waist elastics 69, 72 attached to the front and rear waist members 64, 65 serve to elasticize these front and rear waist members 64, 65 in the transverse direction X. The front and rear waist members 64, 65 may be joined together along respective side edges thereof to form an annular waist-opening.

The crotch member 66 includes a topsheet 73 lying on the side facing the wearer's body and a backsheet 74 lying on the side facing the wearer's garment. The backsheet 74 of the crotch member 66 may be opposed to and joined to the respective inner sheets 67, 70 of the front and rear waist members 64, 65 to obtain a pants-shape as a whole. The crotch member 66 may be joined to the front and rear waist members 64, 65 by the intermediary of adhesive regions (not shown) defined, for example, by appropriate adhesives. The topsheet 73 may be formed of a liquid-pervious fibrous nonwoven fabric and the backsheet 74 may be formed of a liquid-impervious but air-permeable film.

A liquid-absorbent core 75 is attached between the topsheet 73 and the backsheet 74. The core 75 may be formed, for example, from a mixture of fluff pulp fibers and super-absorbent polymer particles wrapped with a tissue paper.

The topsheet 73 includes a pair of stretch sheets 59 attached to the body-facing side of the topsheet 73 so that these stretch sheets 59 may be spaced from each other in the transverse direction X. As the stretch sheet 59, the stretch sheet 59 obtained by the above-described nozzle assembly may be used. Specifically, the stretch sheet 59 includes the first and second sheets 53, 54 formed of a fibrous nonwoven fabric and elastics 2 interposed between these sheets 53, 54 wherein the elastics 2 extend in the longitudinal direction Y and attached to the sheets 53, 54 under tension and in a contractible fashion. The stretch sheet 59 is elasticized in the longitudinal direction Y. The stretch sheets 59 and the topsheet 73 are joined to each other only along respective outer side edges 55 of the paired stretch sheets 59 so that respective inner side edges 56 of these stretch sheets 59 are free to be spaced from the topsheet 73.

With such diaper 60 put on the wearer's body, the respective inner side edges 56 of the paired stretch sheets 59 are spaced upward from the topsheet 73 in response to contraction of the elastics 2 included in the stretch sheets 59. In this way, a pair of leakage-barrier cuffs is formed. The inner side edges 56 are spaced upward from the topsheet 73 to the positions in the vicinity of the wearer's inguinal regions and thereby prevent body waste such as urine from leaking out of the diaper 60. The elastics 2 are not present in the vicinity of the cut edges 51 as a result of so-called cut-back and therefore the regions in the vicinity of the cut edges 51 is free from any significant affection of elastics' contraction and substantially free from getting wrinkled. Consequentially, the stretch sheets 59 can be joined to the topsheet 73 over a relatively large area and with correspondingly high reliability.

In the stretch sheet 59, between each pair of the adjacent elastics 2, the adhesive lines 33 for a web continuously extend in parallel to the elastics 2 to the vicinities of the cut edges 51. With such an arrangement, the first and second sheets 53, 54 should not be peeled off from each other in the vicinities of the cut edges 51. Should these first and second sheets 53, 54 be peeled off in the vicinities of the cut edges 51, the wearer's finger(s) may sometimes be caught between these first and second sheets 53, 54. According to the present embodiment, such apprehension is reliably prevented. In the region other than the vicinities of the cut edges 51, the first and second sheets 53, 54 may be joined to each other by the adhesive lines 33 for a web and by the adhesive lines 32 for elastics.

The non-coated regions are defined between each pair of the respective adjacent adhesive lines 32 for elastics and adhesive lines 33 for a web so that stiffness of the first and second sheets 53, 54 may be restricted and thereby undesirable irritation experienced by the wearer's skin can be alleviated. Furthermore, these non-coated regions 34 defined between the respective adjacent adhesive lines 32, 33 have the air-permeability free from interruption by the adhesive and contribute to prevention of uncomfortable stuffiness which would otherwise be generated in the diaper 60.

The stretch sheet 59 may be used not only as leakage-barrier cuffs but also as waist members which define the front and rear waist regions, respectively. Along with the component members in the diaper, the stretch sheet 59 may be used as the component members in the wearing articles other than the diaper as well as panty liners and sanitary napkins. In such cases, various factors such as the number of the elastics 2, the type of adhesive with which elastics are coated and the number of the adhesive lines may be appropriately selected depending on the respective types of wearing articles.

Figure 14:
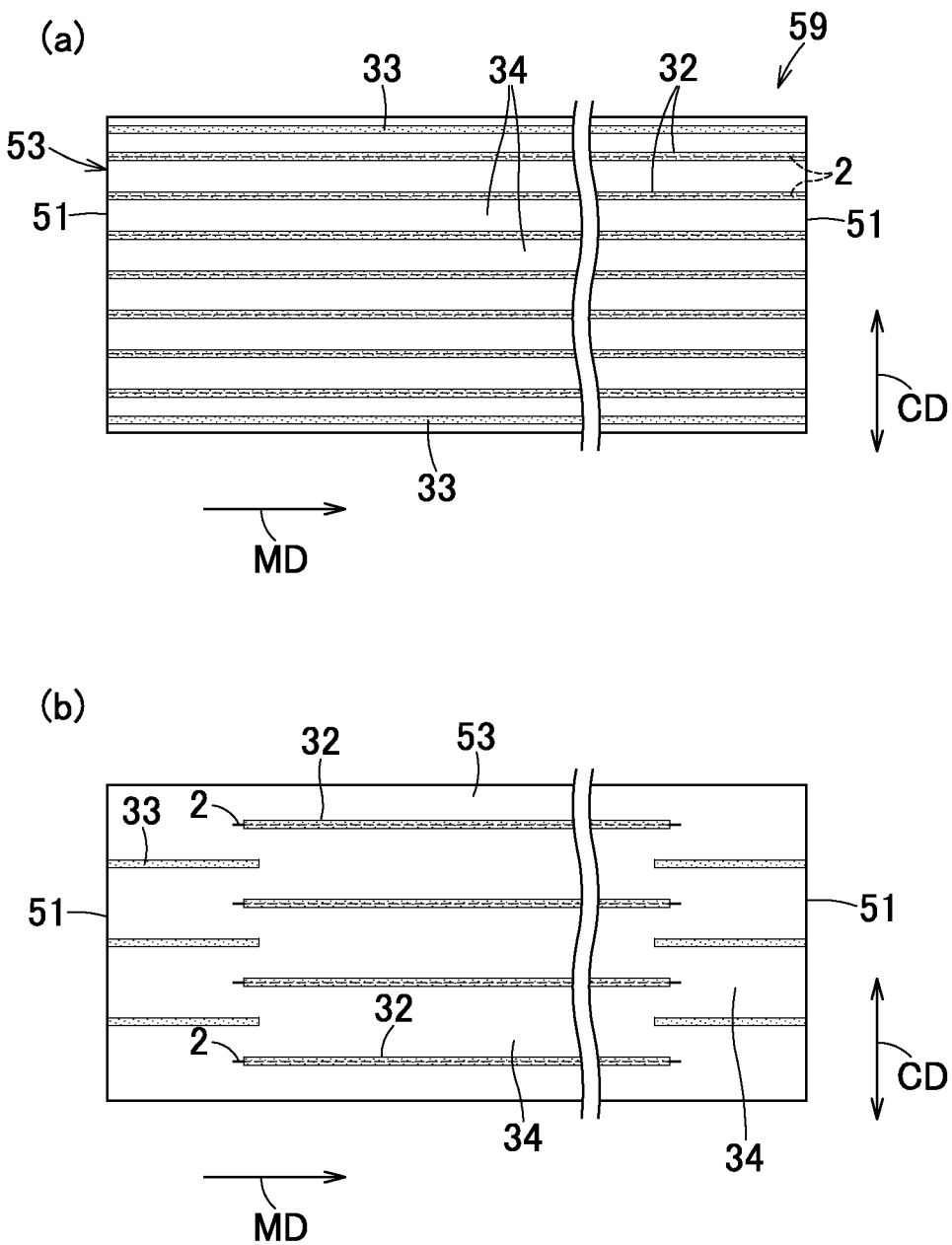
FIG. 14 is a diagram illustrating patterns of adhesive lines and elastics in the composite stretch material.

FIG. 14 illustrates other patterns of elastics and adhesive lines wherein the second sheet 54 is not shown for convenience of illustrating the respective patterns.

FIG. 14 (a) illustrates a pattern in which there are provided only two adhesive lines 33 for a web extending along upper and lower edges opposed to each other in the cross direction CD formed in order to join the first and second sheets 53, 54 to each other and a plurality of the elastics 2 are arranged to extend in the machine direction MD and coated with the adhesive to form a plurality of the adhesive lines 32 for elastics. With such an arrangement, the stretch sheet 59 having a relatively high tensile stress which is, for example, suitable to be used as the waist regions of the diaper may be obtained. In this pattern, the elastics 2 are not cut-back along the cut edges 51 but the adhesive lines 32 for elastics are continuously formed so as to extend from one cut edge to the other cut edge.

FIG. 14 (b) illustrates a pattern in which the adhesive lines 33 for a web functioning to join the first and second sheets 53, 54 to each other are formed intermittently in the machine direction MD. Specifically, the adhesive lines 33 for a web are formed only in the regions in the vicinities of the cut edges 51 but not formed between these two regions. The elastics 2 and the adhesive lines 32 for elastics are provided and formed in the regions in which no adhesive lines 33 for a web are formed as viewed in the machine direction MD. In other words, the adhesive lines 32 for elastics are intermittently formed in the machine direction MD and the sheets 53, 54 may be cut in the regions having none of the adhesive lines 32 for elastics, more specifically, may be cut-back to obtain elastics 2 arranged as has been described.

The adhesive lines 32 for elastics are formed so as to be spaced apart from imaginary extensions of the adhesive lines 32 for a web in the cross direction CD. In other words, each of the adhesive lines 32 for elastics is formed between each pair of the adjacent imaginary extensions of the adhesive lines 32 for a web. The adhesive lines 32 for elastics may be spaced apart from the adhesive lines 33 for a web in the cross direction CD in this manner to enlarge the area of the non-coated regions.

The patterns in which the adhesive lines 32 for elastics and the adhesive lines 33 for a web are formed are not limited to those as have been described above so long as these adhesive lines 32, 33 extend in parallel and the non-coated regions 34 are defined between each pair of the adjacent adhesive lines 32, 33.

The terms "first" and "second" used in the specification and the appended Claims should be construed to be used for the purpose of merely discriminating elements and/or positions of same appellation. In addition, one of the first direction and the second direction should be construed to mean the machine direction MD and the other should be construed to mean the cross direction CD.

The invention claimed is:

1. A pants-shaped disposable diaper having a longitudinal direction, a transverse direction, a side facing a wearer's body and a side facing a garment of the wearer and including a front waist member, a rear waist member, a crotch member extending between the front and rear waist members so as to be contiguous to one another in the longitudinal direction, and a pair of composite stretch sheets attached to the body-facing side of the crotch member being spaced from each other in the transverse direction, each of the composite stretch sheets comprising:
   first and second sheets layered on one another; and
   elastics attached under tension and in a contractible manner between the first and second sheets, wherein:
   each of the stretch composite sheets further comprise:
   adhesive lines for a web adapted to join the first and second sheets together and extending in the longitudinal direction; and
   adhesive lines for elastics each extending in the longitudinal direction in parallel to the adhesive lines for elastics and overlapping with elastics, wherein
   the adhesive lines for a web and the adhesive lines for elastics are spaced one from another in the transverse direction to define non-coated regions coated with no adhesive between the adhesive lines for a web and the adhesive lines for elastics,
   each of the stretch composite sheets is joined to the body-facing side of the crotch member along an outer side edges of the stretch composite sheets so that an inner side edge of the stretch composite sheets is free to be spaced from the body-facing side of the crotch member,
   when the diaper is in use, the inner side edges of the stretch composite sheets are spaced upward from the crotch member in response to contraction of the elastics included in the stretch composite sheets and thereby a pair of leakage-barrier cuffs is formed,
   each of the stretch composite sheets has opposite ends spaced apart from each other in the longitudinal direction,
   the adhesive lines for a web continuously extend in the longitudinal direction between the opposite ends of the stretch composite sheets,
   the elastics extend spaced apart from the opposite ends of the stretch composite sheets in the longitudinal direction,
   at least one adhesive line for elastics lies next to the outer side edge of the stretch composite sheets, and
   at least one adhesive line for elastics lies next to the inner side edge of the stretch composite sheets.

2. A pants-shaped disposable diaper of claim 1, wherein:
   the adhesive lines for a web are arranged only on the opposite ends of the stretch composite sheets,
   the opposite ends of the stretch composite sheets are spaced apart from each other in the longitudinal direction, and
   the adhesive lines for elastics are arranged only on a middle zone of the stretch composite sheets located between the opposite ends.

* * * * *